US010071000B2

(12) United States Patent
Umemoto et al.

(10) Patent No.: US 10,071,000 B2
(45) Date of Patent: Sep. 11, 2018

(54) ABSORBENT ARTICLE

(71) Applicant: DAIO PAPER CORPORATION, Ehime (JP)

(72) Inventors: Kaori Umemoto, Tochigi (JP); Yoko Suzuki, Tochigi (JP)

(73) Assignee: DAIO PAPER CORPORATION, Ehime (JP)

( * ) Notice: Subject to any disclaimer, the term of this patent is extended or adjusted under 35 U.S.C. 154(b) by 289 days.

(21) Appl. No.: 15/030,401

(22) PCT Filed: Nov. 5, 2014

(86) PCT No.: PCT/JP2014/079311
§ 371 (c)(1),
(2) Date: Apr. 19, 2016

(87) PCT Pub. No.: WO2015/068718
PCT Pub. Date: May 14, 2015

(65) Prior Publication Data
US 2016/0250084 A1    Sep. 1, 2016

(30) Foreign Application Priority Data

Nov. 5, 2013 (JP) ................. 2013-229051

(51) Int. Cl.
*A61F 13/15* (2006.01)
*A61F 13/533* (2006.01)
(Continued)

(52) U.S. Cl.
CPC ...... *A61F 13/533* (2013.01); *A61F 13/49001* (2013.01); *A61F 13/5116* (2013.01); *A61F 13/51108* (2013.01)

(58) Field of Classification Search
CPC .............. A61F 13/533; A61F 13/49001; A61F 13/51108; A61F 13/5116
(Continued)

(56) References Cited

U.S. PATENT DOCUMENTS 6,563,013 B1* 5/2003 Murota ............... A61F 13/4704
604/379
8,871,123 B2* 10/2014 de Carvalho ..... A61F 13/15658
264/119

(Continued)

FOREIGN PATENT DOCUMENTS

JP    2002-531172    9/2002
JP    2003-038555    2/2003
(Continued)

OTHER PUBLICATIONS

International Search Report dated Jan. 27, 2015.

*Primary Examiner* — Jacqueline Stephens
(74) *Attorney, Agent, or Firm* — IPUSA, PLLC (57) ABSTRACT

An incontinence pad includes an absorbent body provided between a liquid permeable topsheet and a backsheet, a concave groove formed in a surface of the absorbent body on the liquid permeable topsheet side and extending along an approximately longitudinal direction of the groove, and a highly compressed portion formed in a bottom surface of the concave groove. The highly compressed portion includes a sloping element in a unit portion formed by dividing the concave groove in a longitudinal direction thereof and crossing the concave groove from one side edge to the other side edge, and is formed into a pattern obtained by repeatedly inverting the highly compressed portion of the unit portion in the longitudinal direction.

7 Claims, 6 Drawing Sheets

(51) Int. Cl.
*A61F 13/49* (2006.01)
*A61F 13/511* (2006.01)

(58) Field of Classification Search
USPC .......................... 604/378, 379, 380, 385.01
See application file for complete search history.

(56) References Cited

U.S. PATENT DOCUMENTS

| | | | |
|---|---|---|---|
| 2012/0059342 A1 | 3/2012 | Kinoshita et al. | |
| 2015/0057627 A1* | 2/2015 | Noda | A61F 13/472 604/367 |
| 2015/0282997 A1* | 10/2015 | Arizti | A61F 13/51113 604/378 |

FOREIGN PATENT DOCUMENTS

| | | |
|---|---|---|
| JP | 2003-265518 | 9/2003 |
| JP | 2008-173247 | 7/2008 |
| JP | 2009-112590 | 5/2009 |
| JP | 2010-233839 | 10/2010 |
| WO | 00/32145 | 6/2000 |

* cited by examiner

FIG.10

# ABSORBENT ARTICLE

TECHNICAL FIELD

The present invention mainly relates to an absorbent article used in incontinence pads, sanitary napkins, panty liners, medical pads, toiletries, disposal diapers and the like, and an absorbent article including an absorbent body having a concave groove formed in a top surface thereof along a longitudinal direction thereof.

BACKGROUND ART

In conventional absorbent articles, an absorbent body is provided between a liquid impermeable backsheet, such as a polyethylene sheet or a non-woven fabric made of laminated polyethylene sheets, and a liquid permeable topsheet, such as a non-woven fabric or a permeable plastic sheet.

This kind of absorbent article has been improved many times, and a variety of absorbent articles, in particular, such as a light incontinence pad, has been proposed that have a concave groove formed in its top surface along a longitudinal direction thereof and functions as a urine temporary storage and distributing unit for receiving urine surging out at one time in a small area and rapidly distributing the received urine.

For example, Patent Document 1 describes an absorbent article that includes an upper absorbent layer provided on a skin-contacting side and a lower absorbent layer provided on a non-skin-contacting side. The upper absorbent layer and the lower absorbent layer form a middle high portion that has a groove formed in the skin contacting side and extending in the longitudinal direction of the absorbent article. The groove is an opening portion penetrating through the upper absorbent layer, and the lower absorbent layer is located under the lower surface of the upper absorbent layer so as to form a bottom surface of the opening portion.

Moreover, Patent Document 2 describes an absorbent article that includes an absorbent layer including a lower absorbent layer and an upper absorbent layer, stacked on the lower absorbent layer, that have different areas from each other so as to form a step portion having a difference in level. A concave portion is formed in a topsheet and the absorbent layer together so as to extend in a longitudinal direction of the absorbent article. The concave portion is continuously formed throughout the upper portion and the lower portion including the step portion while passing the center of the absorbent layer in a width direction of the absorbent article without being interrupted by the step portion of the absorbent layer.

Furthermore, Patent Document 3 discloses an absorbent article that has an embossed groove whose bottom surface has highly compressed portions extending from an inner edge toward an outer edge but not reaching the outer edge and intermittently arranged in a longitudinal direction of the groove, and highly compressed portions extending from the outer edge toward the inner edge but not reaching the inner edge and intermittently arranged in the longitudinal direction of the groove so that the highly compressed portions formed from the inner edge and the highly compressed portions formed from the outer edge are alternately arranged in the longitudinal direction of the groove, in order to prevent the embossed groove portion from hardening and a body fluid in the embossed groove from spreading.

RELATED ART DOCUMENTS

Patent Documents

Patent Document 1: Japanese Laid-Open Patent Application Publication No. 2009-112590
Patent Document 2: Japanese Patent No. 5105884
Patent Document 3: Japanese Laid-Open Patent Application Publication No. 2003-265518

SUMMARY OF THE INVENTION

Problem to be Solved by the Invention

In the absorbent articles described in Patent Documents 1 and 2, because the concave grooves are just provided and the absorbent bodies are not present in the concave grooves, the stiffness of the concave grooves is low. Accordingly, the concave grooves are likely to become deformed when compressed by legs from both sides in the width direction while being worn, and such deformation of the concave grooves undermine the efficacy of temporarily storing the body fluid and distributing the body fluid.

Also, the absorbent article of Patent Document 3 increases the stiffness of the embossed groove to some degree and has an effect of reducing the deformation due to compression by legs to some degree because the highly compressed portions extending from one edge toward the other edge without retching the other edge of the embossed groove are provided, but the highly compressed portions are not sufficiently formed to have an adequate pattern to prevent the deformation. In addition, because the highly compressed portions are not formed into a pattern that causes the flow of the body fluid to be generated along the longitudinal direction of the embossed groove, the body fluid is unlikely to distribute along the longitudinal direction of the groove when used in the incontinence pad that needs to absorb large amounts of body fluid in a wider range.

Therefore, in response to the above problems, there is provided an absorbent article that prevents the deformation of the concave groove while being worn and facilitates the diffusion of the body fluid in the longitudinal direction of the groove.

Means for Solving the Problem

To solve the above problem, according to claim 1 of the present invention, there is provided an absorbent article including an absorbent body provided between a liquid permeable topsheet and a backsheet, a concave groove formed in a surface of the absorbent body on the liquid permeable topsheet side and extending along an approximately longitudinal direction of the groove, and a highly compressed portion formed in a bottom surface of the concave groove, wherein the highly compressed portion includes a slanted element in a unit portion formed by dividing the concave groove in a longitudinal direction thereof, and is formed by substantially crossing the concave groove from one side edge to the other side edge and is formed into a pattern obtained by repeatedly inverting the highly compressed portion of the unit portion in the longitudinal direction.

In the above invention as recited in claim 1, as the pattern of the highly compressed portion formed in the bottom surface of the concave groove, in the unit portion obtained by dividing the concave groove in the longitudinal direction thereof, the pattern includes a slanted element extending in a width direction of the groove and sloping in the length direction of the groove, and the pattern is formed by substantially crossing from one side edge to the other side edge of the concave groove and by repeatedly inverting the highly compressed portion of the unit portion in the longitudinal direction of the groove. This causes the slanted element of the highly compressed portion to be arranged in a zigzag manner so that the slanted element substantially crosses in the width direction of the concave groove relative to the longitudinal direction, thereby improving stiffness of the concave groove. Accordingly, when compressed by legs from both sides in the width direction while being worn, a deformation of the concave groove can be prevented, and an effect of temporarily storing and distributing body fluids can be maintained. Moreover, because the zigzag highly compressed portion along the longitudinal direction of the groove is formed in the bottom surface of the concave groove, the body fluid is easily distributed along the longitudinal direction of the groove by being led by the highly compressed portion, and the body fluid surging out at one time can be absorbed by a broader range of the absorbent body. The expression "substantially crosses" is intended to include cases where the highly compressed portion is formed as a discontinuous line such as a dotted line or a line having a gap in the middle of the line in addition to cases where the highly compressed portion is formed as a continuous line.

As the present invention according to claim 2, there is provided the absorbent article as claimed in claim 1, wherein the slanted element is composed of a straight line, a curved line or a combination thereof.

The above invention described in claim 2 specifies that the slanted element can be composed of a straight line, a curved line or a combination thereof. When focusing on only the slanted element of the highly compressed portion, the overall pattern is composed of a zigzag polygonal line along the longitudinal direction of the groove if the slanted element is composed of the straight line, and is composed of a wavy line or a continuous provided line of an approximately semicircular arc if the slanted element is composed of the curved line.

As the present invention according to claim 3, there is provided the absorbent article as claimed in claim 1 or 2, wherein the highly compressed portion includes an arch element extending from both ends of the slanted element or neighborhoods thereof in approximately the longitudinal direction and formed into an curved shape protruding outward in the width direction.

In the above invention as recited in claim 3, because the highly compressed portion extends in approximately the longitudinal direction of the groove from both ends of the slanted element or the neighborhoods thereof, and includes the arch element formed into the curved shape protruding outward in the width direction of the groove, when receiving a leg pressure from both sides while being worn, the arch element generates a resistance force against an external force in the width direction and acts to improve the stiffness of the concave groove.

As the present invention according to claim 4, there is provided the absorbent article as claimed in any of claims 1 to 3, wherein the slanted element is composed of a single line or a double line.

In the above invention as recited in claim 4, when the slanted element is composed of the double line, the stiffness of the concave groove can be further improved, and the diffusion of the body fluid can be performed more smoothly.

As the present invention according to claim 5, there is provided the absorbent article as claimed in any of claims 1 to 4, wherein the absorbent body has an absorbent body concave portion formed in its surface on the liquid permeable topsheet side along a longitudinal direction of the absorbent article across a range of the longitudinal direction including a body fluid expelling area, and an embossed part including the highly compressed portion is formed in and along the absorbent body concave portion.

In the above invention as recited in claim 5, the absorbent body concave portion is preliminarily formed in the absorbent body without being compressed, and then the embossed part including the highly compressed portion is formed in the absorbent body concave portion over the length of the absorbent body concave portion. The absorbent body concave portion can more substantially reduce an elevation of the bottom part thereof when absorbing a body fluid than an absorbent body concave portion having a bottom part formed with a high-density polymer or pulp by being formed by compressing the absorbent body, and can maintain a state of the concave groove after absorbing the body fluid.

As the present invention according to claim 6, there is provided the absorbent article as claimed in claim 5, wherein the embossed part is provided so as to have a width smaller than the width of the absorbent body concave portion.

As the present invention according to claim 7, there is provided the absorbent article as claimed in claim 5, wherein the embossed part is provided so as to have a width larger than the width of the absorbent body concave portion, and high-density areas obtained by compressing the absorbent body are formed on both sides of the absorbent body concave portion by providing the embossed part.

The embossed part may be provided so as to have a width narrower than a width of the absorbent body concave portion like the invention as recited in claim 6, or may be provided so as to have a width wider than a width the absorbent body concave portion like the invention as recited in claim 7. In particular, when the embossed part is wider than the width of the absorbent body concave portion as recited in the latter, the high-density areas obtained by compressing the absorbent body are formed on both sides of the bottom part of the absorbent body concave portion, and the stiffness of the concave groove can be increased. Also, because a density gradation that increases a fiber density from the center toward both sides is formed in the bottom portion of the concave groove, the absorbed body fluid is easily distributed from the center toward both sides by a capillary action, and the body fluid in the concave groove can be quickly transferred toward the absorbent body.

Advantageous Effect of the Invention

As described above, according to the present invention, in an absorbent article having a concave groove formed in a top surface of an absorbent body along a longitudinal direction thereof, a deformation of the concave groove can be prevented while being worn, and a body fluid is likely to diffuse in the longitudinal direction of the groove.

EMBODIMENTS FOR IMPLEMENTING THE INVENTION

In the following, embodiments of the present invention are described with reference to the accompanying drawings.

Basic Configuration of Incontinence Pad 1

Figure 1:
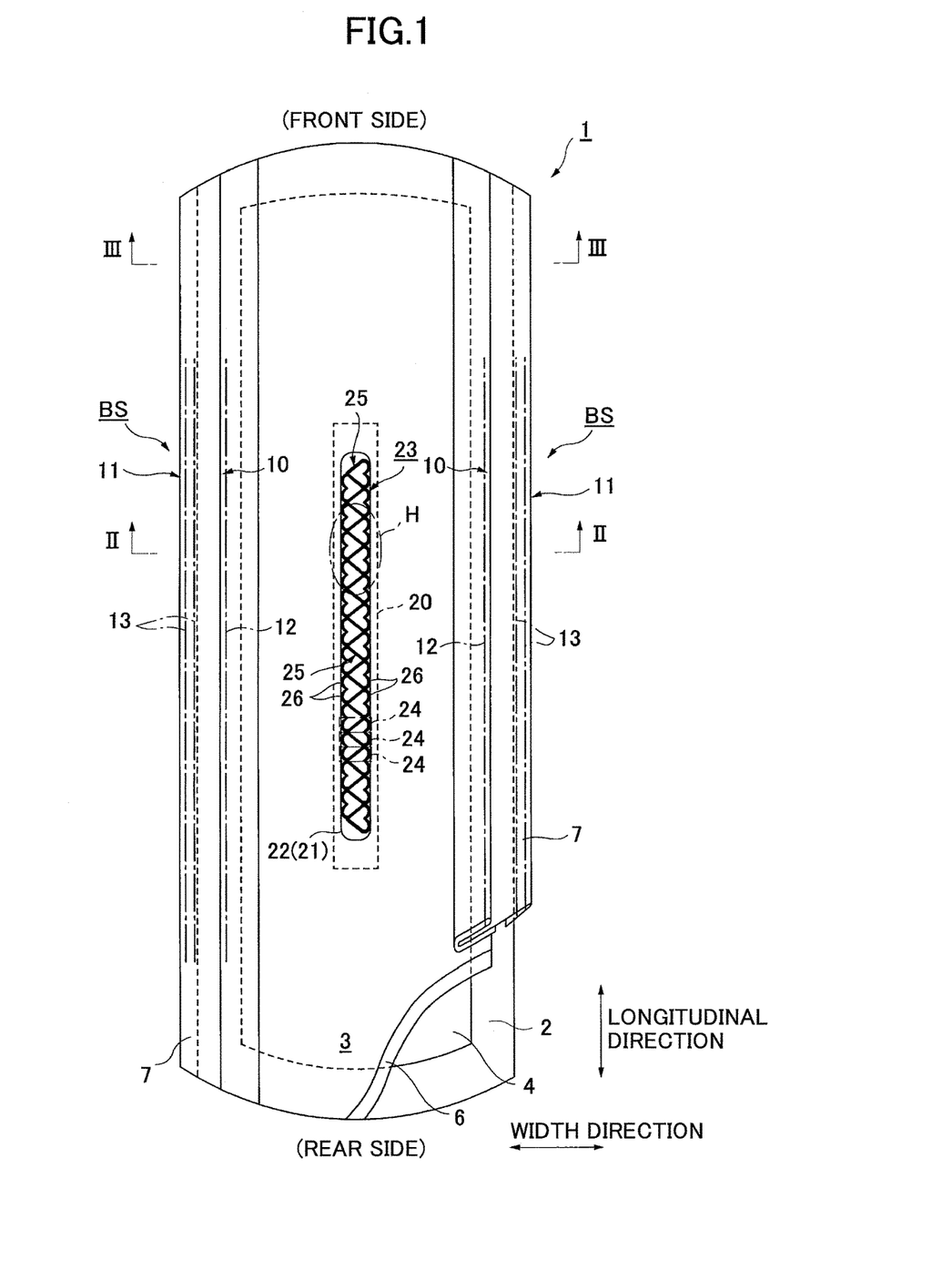
FIG. 1 is a partial cutaway diagram of an incontinence pad 1 of the present invention.
Figure 2:
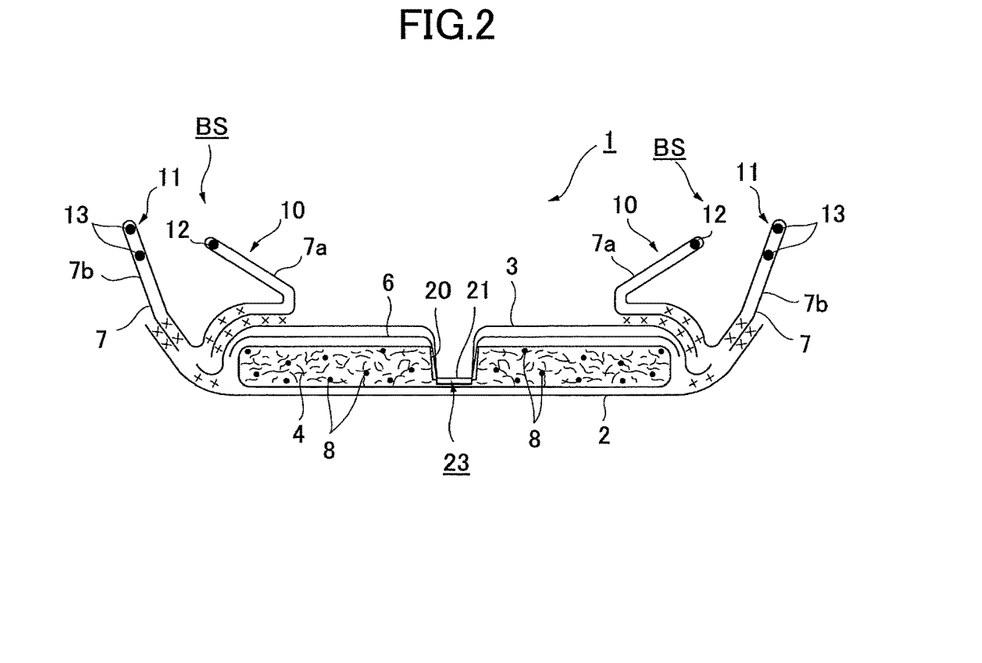
FIG. 2 is a cross-sectional view on taken along a II-II line.
Figure 3:
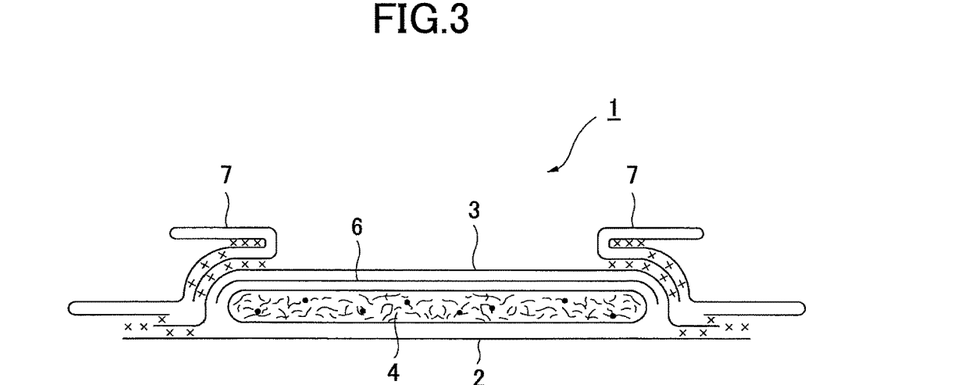
FIG. 3 is a cross-sectional view on taken along a III-III line.

As illustrated in FIG. 1 through FIG. 3, an incontinence pad 1 of the present invention is mainly constituted of a liquid impermeable backsheet 2 made of polyethylene, a liquid permeable topsheet 3 that allows urine and the like to rapidly permeate, an absorbent body 4 made of cotton-like pulp, synthetic pulp or the like and provided between both the sheets 2 and 3, a hydrophilic second sheet 6 disposed between the liquid permeable topsheet 3 and the absorbent body 4 as necessary, and non-woven fabric sides 7 forming a matched pair of standing gathers BS that protrude toward a skin side in a predetermined zone including at least a body fluid expelling area H in the longitudinal direction while standing from approximately side edge parts of the absorbent body 4. Around the absorbent body 4, the outer end portions of the liquid impermeable backsheet 2 and the liquid permeable topsheet 3 are bonded with an adhesive such as a hot-melt adhesive or an adhesive means such as a heat seal and the like at end portions in the longitudinal direction, and the liquid impermeable backsheet 2 laterally protruding from the absorbent body 4 and the side non-woven-fabric are bonded with the adhesive such as the hot-melt adhesive or the adhesive means such as the heat seal and the like at the edge portions on both sides. The absorbent body 4 can be surrounded by an encapsulating sheet (not illustrated) such as a crepe paper sheet and a non-woven fabric to retain a shape and to improve diffusivity thereof.

Hereinafter, the structure of the incontinence pad 1 is further described in more detail. A sheet material having at least water shielding properties such as polyethylene, polypropylene or the like is used in the liquid impermeable backsheet 2. In addition to this, a non-woven fabric sheet can be also used after ensuring substantial impermeability by providing a waterproof film to cover the non-woven fabric sheet (in this case, the liquid impermeable backsheet is composed of the waterproof film and the non-woven fabric sheet). In recent years, a material having moisture permeability is often preferably used to prevent sweating. A microporous sheet obtained by forming a sheet by melting and kneading inorganic filler in olefin series resin such as polyethylene and polypropylene and then extruding the sheet in one axial direction or two axial directions, is preferably used as the waterproof and moisture permeable sheet material.

Next, a perforated or imperforate non-woven fabric or a porous plastic sheet can be preferably used as the liquid permeable topsheet 3. For example, a regenerated fiber such as rayon and cupra, and a natural fiber such as cotton, can be used as a material fiber forming the non-woven fabric in addition to a synthetic fiber including an olefin series such as polyethylene and polypropylene, a polyester series, a polyamide series and the like. As the non-woven fabric, a non-woven fabric obtained by a proper processing method such as a spun lace method, a spun bond method, a thermal bond method, a melt blown method, and a needle punch method, can be used. Among the processing methods, the spun lace method is superior in terms of great flexibility and drape properties, and the thermal bond method is superior in terms of bulkiness and softness.

The absorbent body 4 is, for example, constituted of an absorbable fiber such as a fluff pulp and superabsorbent polymers 8, and is formed into an approximately oval shape extending long in a longitudinal direction of the pad in a planar shape in the illustrated example. The superabsorbent polymers 8 are, for example, formed into granular powders, and are diffused and mixed into the pulp forming the absorbent body 4.

Chemical pulp obtained from wood, a cellulose fiber such as dissolving pulp, and an artificial cellulose fiber such as rayon and acetate, are cited as examples available for the pulp, and softwood pulp having a fiber length longer than that of hardwood pulp is preferably used in terms of function and price. Although not illustrated, when the absorbent body 4 is surrounded by an encapsulating sheet, as a result, the encapsulating sheet is provided between the liquid permeable topsheet 3 and the absorbent body 4. Thus, an encapsulating sheet having excellent absorbability serves to rapidly distribute the body fluid and to prevent urine and the like from flowing back. The fabric weight per unit area of the pulp is preferably set in a range of 100 $g/m^2$ to 600 $g/m^2$, and further preferably set in a range of 200 $g/m^2$ to 500 $g/m^2$.

For example, a cross-linking polyacrylate, a self-cross-linking polyacrylate, a saponified substance of a cross-linking copolymer of acrylic acid ester and vinyl acetate, a cross-linking substance of a copolymer of isobutylene and maleic anhydride, a cross-linking polysulfonate, and a partially cross-linking substance of a water swellable polymer such as polyethylene oxide and polyacrylamide are cited as examples of the superabsorbent polymer 8. Among the examples, a substance of acryl acid or an acrylate-based substance having a large amount of water absorption and a high absorption speed is preferable. The water-absorbing power (water-absorbing ratio) and the water absorption speed of the superabsorbent polymer having the above-mentioned water absorption performance can be adjusted by adjusting a cross-linking density and a cross-linking density gradient in its manufacturing process. The fabric weight per unit area of the polymer is preferably set in a range of 150 $g/m^2$ to 500 $g/m^2$, and further preferably set in a range of 200 $g/m^2$ to 450 $g/m^2$.

Moreover, a synthetic fiber may be mixed into the absorbent body 4. For example, a polyolefin series such as polyethylene or polypropylene, a polyester series such as polyethylene terephthalate and polybutylene terephthalate, and a polyamide series such as nylon, and a copolymer thereof, or a mixture of two kinds thereof, can be used as the synthetic fiber. Furthermore, a composite fiber such as a core-clad type fiber including a core made of a fiber with a high melting point and a clad made of a fiber with a low melting point, a side-by-side type fiber, and a division type, can be also used. When the synthetic fiber is made of a hydrophobic fiber, it is preferable to treat a surface of the synthetic fiber with a hydrophilic agent so as to have hydrophilic properties to the body fluid.

The second sheet 6 just has to have hydrophilic properties to the body fluid. More specifically, a hydrophilic material that has hydrophilic properties in itself can be used as the second sheet 6 by using the regenerated fiber such as rayon and cupra, and the natural fiber such as cotton. Otherwise, a fiber treated to have the hydrophilic properties by treating a surface of a synthetic fiber including an olefin series such as polyethylene and polypropylene, a polyester series, a polyamide series and the like with a hydrophilic agent, can be used. In addition, the second sheet 6 may include a porous film layer on its back side (the absorbent body 4) to provide tension, and may be laminated with the encapsulating sheet, and further may be made of a material including pulp.

On both sides of the top surface side of the present incontinence pad 1, side non-woven fabrics 7, 7 are respectively provided along the longitudinal direction over the entire length of the incontinence pad 1, and outer parts of the side non-woven-fabrics 7, 7 extend laterally while the liquid impermeable backsheet 2 extends laterally. Side flaps are formed by attaching the laterally extended side non-woven-fabric 7 parts to the laterally extended liquid impermeable backsheet 2 parts with the hot-melt adhesive and the like.

Either water-repellent non-woven fabric or hydrophilic non-woven fabric is used as the side non-woven-fabric 7 depending on the desired function. For example, when regarding a function of preventing urine and the like from permeating or of improving a texture as important, it is preferable to use the water-repellent non-woven fabric such as SSMS, SMS or SMMS coated with water-repellent agent and the like of a silicon series, a paraffin series and an alkyl chromic chloride series. When regarding the absorbability of the body fluid as important, it is preferable to use a hydrophilic non-woven fabric obtained by making a swellable or porous synthetic fiber by a method of polymerizing the synthetic fiber in the presence of a compound having a hydrophilic group, for example, an oxidation product of polyethylene glycol, in the manufacture of the synthetic fiber, or a method of treating the surface with a metallic salt such as stannic chloride to partially dissolve the surface to form a porous surface and then to precipitate a metallic hydroxide on the surface, and then providing the hydrophilic property for the synthetic fiber by using capillary action. A fiber obtained by processing the natural fiber, the synthetic fiber or the regenerated fiber by a proper processing method is available for the side non-woven-fabric 7.

The side non-woven-fabrics 7, 7 are properly folded to form the standing gathers BS of a double structure including the matched pair of inner standing gathers 10, 10 standing from the neighborhood of the edges of the absorbent body 4 toward the skin side, and the matched pair of outer standing gathers 11, 11 that are located outside the inner standing gathers 10, constituted of the liquid impermeable backsheet 2 extending laterally so as to protrude from the absorbent body 4 and the side non-woven-fabrics 7, and formed so as to stand toward the skin side. Here, the standing gather BS may have a single gather structure constituted of only one of the inner standing gather 10 or the outer standing gather 11, or may not be formed into a standing gather shape standing toward the skin side by just providing the side non-woven-fabric 7 without raising it.

The structure of the inner standing gather 10 and the outer standing gather 11 is described below in more detail. As illustrated in FIG. 2, double sheet parts 7a, 7b are respectively formed on the inner side and the outer side in the width direction by folding both sides of the side non-woven-fabric 7 in the width direction. At least one, in the illustrative example, one threadlike elastic stretchable member 12 is fixed at both ends or proper locations in the longitudinal direction, and is provided inside the double sheet part 7a. At least one, in the illustrative example, two threadlike elastic stretchable members 13, 13 are fixed at both ends or proper locations in the longitudinal direction, and are provided inside the double sheet part 7b. By attaching the base edge portion of the double sheet part 7a on the inner side in the width direction to the upper surface of the liquid permeable topsheet 3 provided on a side portion of the absorbent body 4 with a hot-melt adhesive or the like, and attaching the base edge portion of the double sheet part 7b on the outer side in the width direction to the side edge portion of the liquid impermeable backsheet 2 laterally protruding from the absorbent body 4 with the hot-melt adhesive, the inner standing gather 10 standing toward the skin side is formed of the double sheet part 7a on the inner side in the width direction, and the outer standing gather 11 standing toward the skin side is formed of the double sheet part 7b on the outer side in the width direction. Here, as illustrated in FIG. 3, the side non-woven-fabric 7 does not include the threadlike elastic stretchable members 12, 13 at the end portions in the longitudinal direction, and the double sheet part 7a on the inner side in the width direction is attached to the absorbent body 4 with a hot-melt adhesive.

Configuration of Concave Groove

In the incontinence pad 1, a concave groove 22 that allows body fluids to flow therein is formed in the liquid permeable topsheet 3 (the skin surface side) along the longitudinal direction of the pad, and highly compressed portions 23 with a predetermined pattern are formed in a bottom surface of the concave groove 22. The concave groove 22 receives the body fluid expelled on the surface of the liquid permeable topsheet 3 and temporarily stores the body fluid, while facilitating the diffusion of the body fluid in a front-back direction to increase the absorption speed of the body fluid into the absorbent body 4 and to prevent a side leak of the body fluid.

Although the concave groove 22 may be formed by compressing component members from the liquid permeable topsheet 3 to the absorbent body 4 together from the surface of the liquid permeable topsheet 3, as described later, it is preferable to preliminarily form an absorbent body concave portion 20 in the absorbent body 4 and then to form an embossed part 21 by compressing the component members on an upper layer side from the upper surface of the liquid permeable topsheet 3 into the absorbent body 4 along the absorbent body concave portion 20 because the deformation of the concave groove 22 due to compression by the wearer's legs can be prevented.

Figure 4:
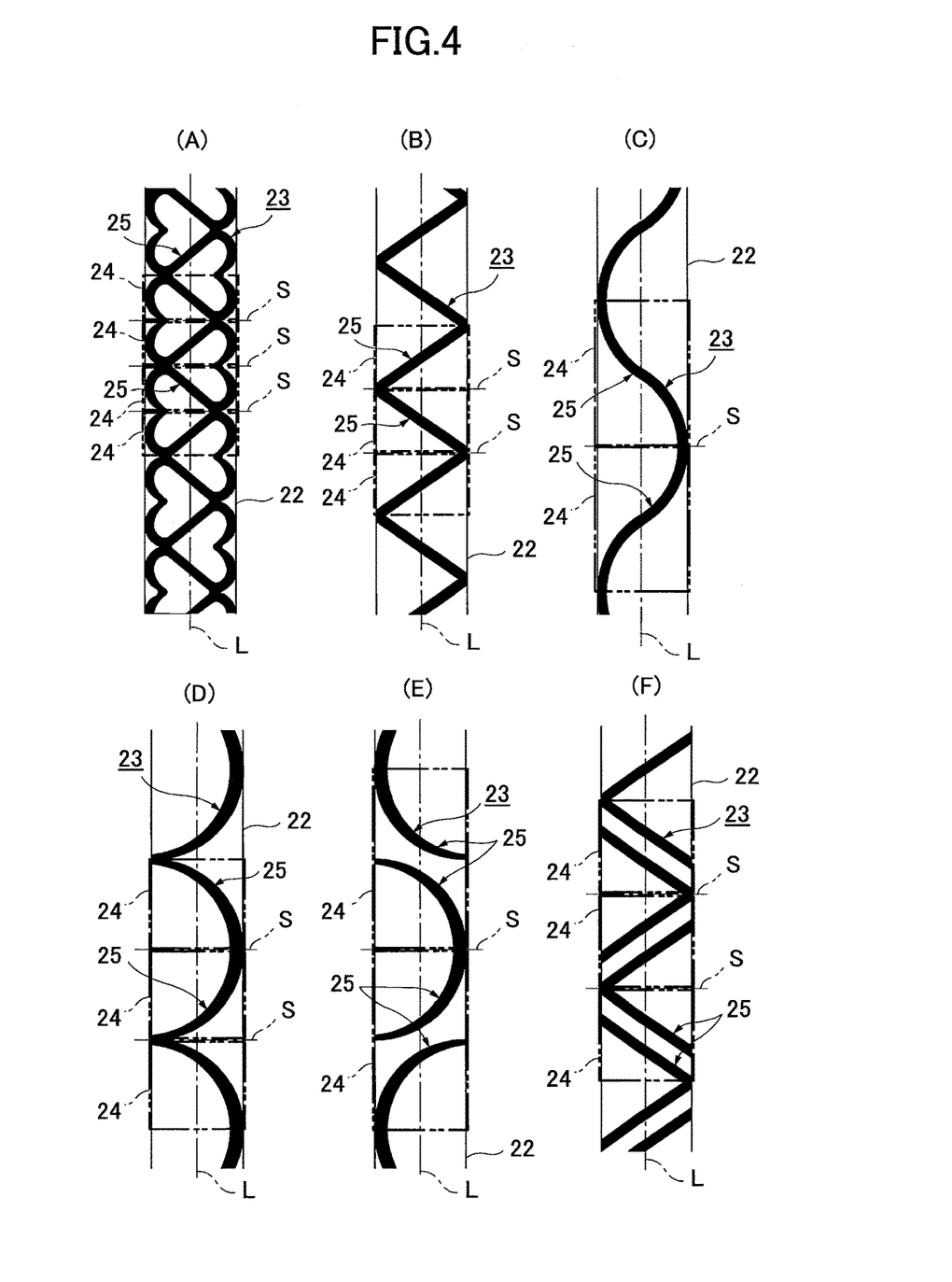
FIGS. 4(A)-(F) are planar patterns of highly compressed portions 23.

The highly compressed portion 23 is a portion compressed more deeply than the surrounding bottom surface of the concave groove, and is formed in the bottom surface of the concave groove 22 in a predetermined pattern. More specifically, as illustrated in FIG. 4, the highly compressed portions 23 include a slanted element 25 extending in a width direction of the groove and sloping in a longitudinal direction of the groove in a hypothetical unit portion 24 obtained by dividing the concave groove 22 in the longitudinal direction of the groove in a planar view, and the slanted element 25 is formed so as to substantially extends from one side edge to the other side edge in the width direction of the groove, and into a pattern obtained by repeatedly inverting the highly compressed portion 23 of the unit portion 24 in the longitudinal direction of the groove. In other words, the slanted element 25 is formed into a pattern including a regular arrangement in which the highly compressed portion 23 is formed in the unit portion 24 and a reversed arrangement in which the regular arrangement is reversed in the longitudinal direction that are alternately arranged along the longitudinal direction of the groove. Here, the expression "the highly compressed portion 23 is substantially formed so as to substantially cross the concave groove 22" is intended to cover both cases where the highly compressed portion 23 is formed in a continuous line that continues from one side edge to the other edge side in the width direction and where the highly compressed portion 23 is formed in a discontinuous line such as a dotted line or intermittent line (see FIG. 5(C)) having disconnected locations in the middle of the line.

Figure 7:
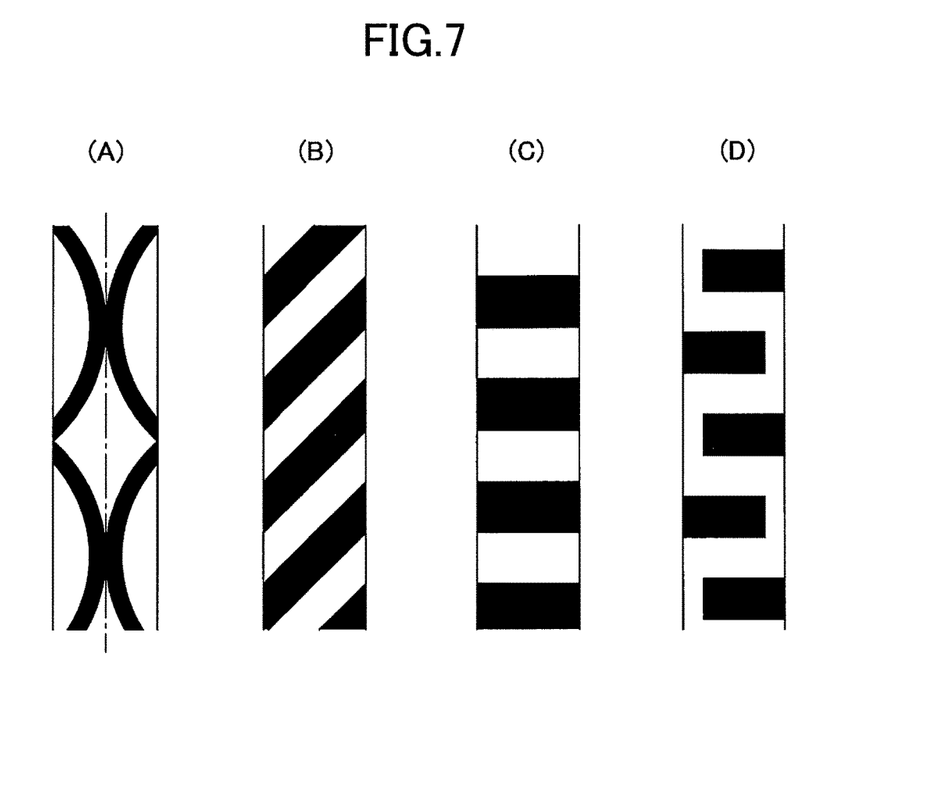
FIGS. 7(A)-(D) are planar patterns of highly compressed portions not corresponding to the present invention.

This causes the slanted element 25 of the highly compressed portion 23 to be arranged in the bottom surface of the concave groove 22 in a zigzag manner along the longitudinal direction thereof, thereby increasing the stiffness of the concave groove 22 against the pressure from both sides in the width direction by allowing the zigzag highly compressed portion 23 to function as a reinforcing element. In other words, the concave groove 22 has a proof stress against a pressure in an oblique direction in addition to the proof stress against the pressure from both sides in the width direction perpendicular to the longitudinal direction of the groove, and can reliably improve the stiffness thereof. Accordingly, even if the leg pressure caused by the complicated movement of the wearer's legs while being worn is applied from both sides, the deformation of the concave groove 22 can be reliably prevented, and the effect of storing body fluid and distributing the body fluid can be maintained. In contrast, for example, as illustrated in FIG. 7(B), when the concave groove 22 is formed into a pattern sloping only in a single direction, although the concave groove 22 is strong enough to bear an external force along the sloping direction, the concave groove 22 is not strong enough to bear an external force in a direction perpendicular to the sloping direction. Moreover, by arranging the slanted element 25 in a zigzag manner, the body fluid is led along the highly compressed zigzag portion 23 formed in the bottom surface of the concave groove 22 along the longitudinal direction thereof, which facilitates the diffusion of the body fluid along the longitudinal direction of the groove and causes the body fluid surging out at one time to be absorbed by a broader range of the absorbent body 4.

As illustrated in FIG. 4, the unit portions 24 are areas provided at regular intervals in the longitudinal direction of the groove, and are formed into rectangular areas surrounded by two parallel lines extending along the width direction of the groove and apart from each other in the longitudinal direction and both side surfaces of the concave groove 22. In each of the unit portions 24, the highly compressed portion 23 extends from one side to the other side in the width direction of the groove. In the adjacent unit areas 24 and 24, the slanted elements 25 of the highly compressed portions 23 are provided to slope in directions opposite to each other in the longitudinal direction of the groove from the border line between the adjacent unit areas 24 and 24.

The above-mentioned expression of "the pattern obtained by repeatedly inverting the highly compressed portion 23 of the unit portion 24 in the longitudinal direction of the groove" means a pattern formed by repeatedly folding the unit portion 24 having a predetermined pattern of the highly compressed portion 23, along lines S extending in the width direction of the pad and passing ends of the unit portion 24 in the longitudinal direction of the groove.

The slanted element 25 is a line extending from one point on one side to another point on the other side in the width direction of the groove so as to cross over the center line L in the longitudinal direction of the concave groove 22, and does not necessarily start from both edges in the width direction of the groove, and may be formed by starting from a point located inside and apart from both edges. The slanted element 25 has a component sloping down to only one side (front side or back side) in the longitudinal direction of the groove in a single unit portion 24, and does not have a component sloping down to the other side opposite to the above-mentioned side in the longitudinal direction of the groove.

Figure 5:
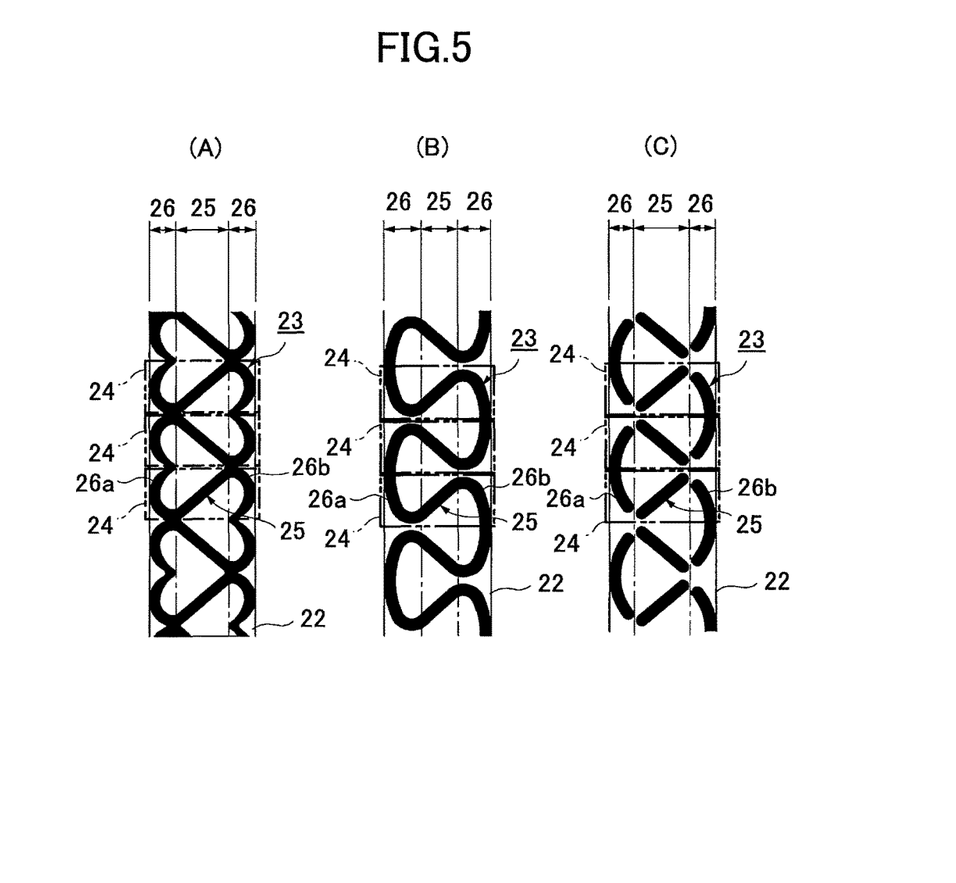
FIGS. 5(A)-(C) are planar patterns of highly compressed portions 23.

As illustrated in FIGS. 4(A), (B), (F) and FIG. 5, the slanted element 25 may be formed into a straight line, or may be formed into a curved line as illustrated in FIGS. 4(C)-(E). Also, although not illustrated in the drawings, the slanted element 25 may be formed into a combination of a straight line and a curved line. When focusing on only the slanted element 25, the overall pattern of the highly compressed portion 23 along the longitudinal direction of the groove is composed of a zigzag polygonal line if the slanted element 25 is composed of a straight line, and the overall pattern of the highly compressed portion 23 along the longitudinal direction of the groove is composed of a wavy line or a continuously provided line of an approximately semicircular arc if the slanted element 25 is composed of a curved line.

As illustrated in FIGS. 4(B)-(F), the highly compressed portion 23 may be composed of only the slanted element 25, or may be composed of a pattern formed by the combination of the slanted element 25 and another element of a highly compressed portion as illustrated in FIG. 5. As illustrated in FIG. 5, each of the highly compressed portions 23 may include arch elements 26 provided extending continuously from both ends of each of the slanted elements 25 or from the neighborhood of both ends of each of the slanted elements 25 apart from both ends in approximately the longitudinal direction of the groove and formed into a curved shape protruding outward in the width direction of the groove. By providing the arch element 26, when the leg pressure is applied from both ends to the concave groove 22 while being worn, the arch element 26 acts to resist this external force, thereby further enhancing the stiffness of the concave groove 22.

As a specific pattern of the highly compressed portion 23 provided with the arch element 26, in an example illustrated in FIG. 5(A), a highly compressed portion 23 is formed into a laterally facing approximately S-shape in one unit portion 24 by being constituted of a slanted element 25 extending diagonally from one side to the other side in the width direction and the longitudinal direction of the groove, a semicircular-arc-shaped one-side arch element 26a continuously extending from an end of the slanted element 25 on one side in the width direction to the other end in the approximately longitudinal direction and protruding outward in the width direction, and a semicircular-arc-shaped other-side arch element 26b continuously extending from the end of the slanted element 25 on the other side in the width direction to the other end in the approximately longitudinal direction and protruding outward in the width direction. The overall pattern of the groove formed by repeatedly inversing the highly compressed portion 23 in the unit portion 24 has an exterior appearance of including laterally facing heart shapes alternately arranged to face opposite to each other. Accordingly, the highly compressed portion 23 excels in design and is easy to exert a resistance force against the external force from both sides in the width direction of the groove because the arch elements 26a, 26b are finely formed. Moreover, as illustrated in FIG. 5(B), two of the arch elements 26 composed of the adjacent unit portions 24, 24 may constitute a single curved shape protruding toward both sides of one width direction of the groove. Furthermore, as illustrated in FIG. 5(C), the slanted element 25 and the arch element 26 may be apart from each other.

As illustrated in FIGS. 4(A)-(D), the slanted element 25 may be formed into a single line in one unit portion 24, or may be formed into a double line apart from each other in the longitudinal direction of the groove as illustrated in FIGS. 4(E), (F). When forming the slanted element 25 into the double line, the stiffness of the concave groove 22 is more reliably enhanced, and the diffusion of the body fluid becomes more smoothly. As illustrated in FIG. 4(E), when the slanted elements 25 are formed into arc-like curved lines, by arranging the slanted elements 25 so that the arcs face in a back-to-back manner, the stiffness can be increased uniformly against the leg pressure from both sides because the semicircular arcs are alternately arranged to face in the opposite direction as a whole. In contrast, when the slanted elements 25 are formed into arc-like curved lines in parallel with each other, the stiffness difference is caused because figures with the same shape do not alternately appear along the longitudinal direction of the groove, which is not preferable.

Figure 6:
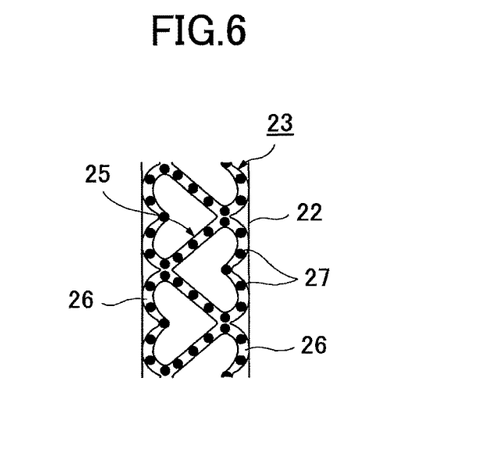
FIG. 6 is a planar pattern of a highly compressed portion 23 when providing a compressed portion 27.

As illustrated in FIG. 6, compressed portions 27, 27 . . . that are deeper than the highly compressed portion 23 may be formed in the highly compressed portion 23. In the illustrated example, the compressed portions 27 are configured to be a plurality of dots formed at predetermined intervals. The breakage of the liquid permeable topsheet 3 can be prevented by providing the compressed portions 27, and the stiffness of the concave groove 22 can be further improved.

Here, when unfavorable patterns of the high compressed portions are illustrated, as illustrated in FIG. 7(A), the highly compressed portions formed into a pattern that does not cross a straight line along the longitudinal direction of the groove (the center line in the longitudinal direction) are not preferable because the bottom part of the concave groove is liable to fold at the straight line part. Moreover, as illustrated in FIG. 7(B), the highly compressed portions formed into a pattern sloping down to a constant direction are not preferable because the stiffness against the pressure in the width direction of the groove decreases. As illustrated in FIG. 7(C), a pattern formed into lines in parallel with the width direction is not preferable because the diffusion of the body fluid in the longitudinal direction of the groove is unlikely to occur. Furthermore, as illustrated in FIG. 7(D), the highly compressed portions formed into a pattern including the highly compressed portions extending from one side edge toward the other side edge without reaching the other side edge in the width direction and the highly compressed portions extending from the other side edge toward the one side edge without reaching the one side edge in the width direction that are alternately arranged, are not preferable because the stiffness against the pressure in the width direction is low and the diffusion of the body fluid in the longitudinal direction of the groove is unlikely to occur.

Next, a means of further preventing the deformation of the concave groove 22 when an external force is applied and facilitating the preservation of the shape of the concave groove 22 even after absorbing the body fluid will be described below. As the means for the purpose, as illustrated in FIG. 2, the absorbent body 4 includes the absorbent body concave portion 20 formed in a surface on the liquid permeable topsheet 3 (surface on the skin side) along the longitudinal direction of the pad across a range including the body fluid expelling area H in the longitudinal direction without being compressed.

Figure 8:
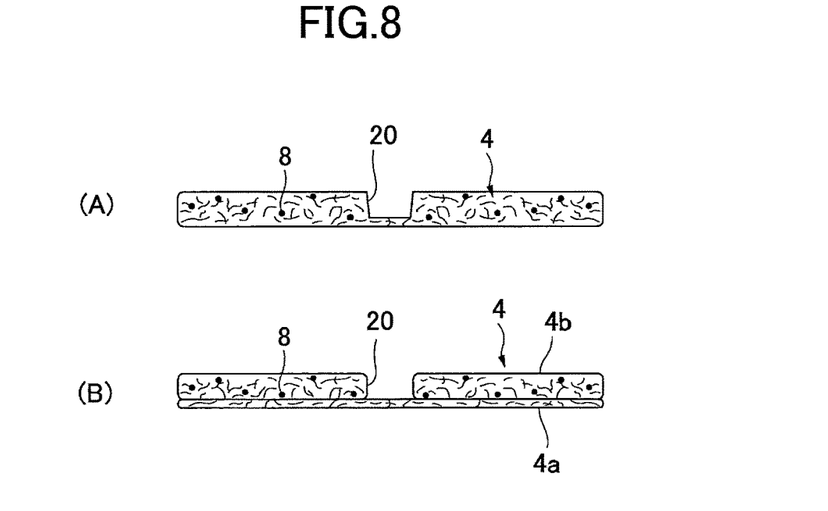
FIG. 8 is a cross-sectional view of an absorbent body 4.

The absorbent body concave portion 20 is a non-through-hole type concave portion with a bottom surface that is hollowed toward the liquid impermeable backsheet 2 so as to be lower than the surrounding absorbent body. For example, as illustrated in FIG. 8, the absorbent body concave portion 20 is formed by (A) fiber stacking, or (B) stacking an upper layer absorbent body 4b having an opening at a location corresponding to the absorbent body concave portion 20 on a lower layer absorbent body 4a formed as thick as the bottom part of the absorbent body concave portion 20 without using the compression.

In a part of the absorbent body 4 provided at the bottom of the absorbent body concave portion 20 (part on the liquid impermeable backsheet 2, part on the non-skin side), the mass per unit area of the pulp is set in a range of 70 $g/m^2$ to 210 $g/m^2$, and preferably in a range of 90 $g/m^2$ to 190 $g/m^2$. The mass per unit area of the polymer in the same part is set in a range of 60 $g/m^2$ to 200 $g/m^2$, and preferably in a range of 80 $g/m^2$ to 180 $g/m^2$.

Then, the liquid permeable topsheet 3 and the second sheet 6 as necessary, are stacked on the surface of the skin side of the absorbent body 4 having the absorbent body concave portion 20, and the embossed part 21 including the highly compressed portion 23 is provided in the absorbent body concave portion 20 along the absorbent body concave portion 20 by embossing the absorbent body 4 from the upper surface side (skin side) of the liquid permeable topsheet 3.

In order to provide the embossed part 21, at least the liquid permeable topsheet 3 and the absorbent body 4 are stacked and embossed from the top surface side of the liquid permeable topsheet 3. At this time, the embossed part 21 may be formed narrower than the absorbent body concave portion 20 by embossing the liquid permeable topsheet 3 and the absorbent body 4 with a tip that is narrower than the width of the absorbent body concave portion 20. By making the embossed part 21 narrower than the width of the absorbent body concave portion 20 and providing the absorbent body concave portion 20 in the absorbent body 4, corner portions formed in the surface on the skin side of the absorbent body 4 get crushed and get rounder, and a cross section having curved sloping side surfaces swelling inward of the concave groove decreases in width from the upper surface toward the non-skin side, is formed as a whole. Hence, even if the width of the groove becomes narrower due to an applied external force, because the concave groove does not immediately and completely disappear but gradually becomes narrower from the bottom side, a certain level of absorption performance can be maintained even though the absorption of the body fluid slightly decreases.

Like the present example, when the second sheet 6 is provided between the liquid permeable topsheet 3 and the absorbent body 4, the embossed part 21 is provided in the liquid permeable topsheet 3 laminated on the second sheet 6. In addition, when the absorbent body 4 is surrounded by an encapsulating sheet, the encapsulating sheet is also embossed together with the liquid permeable topsheet 3.

Figure 9:
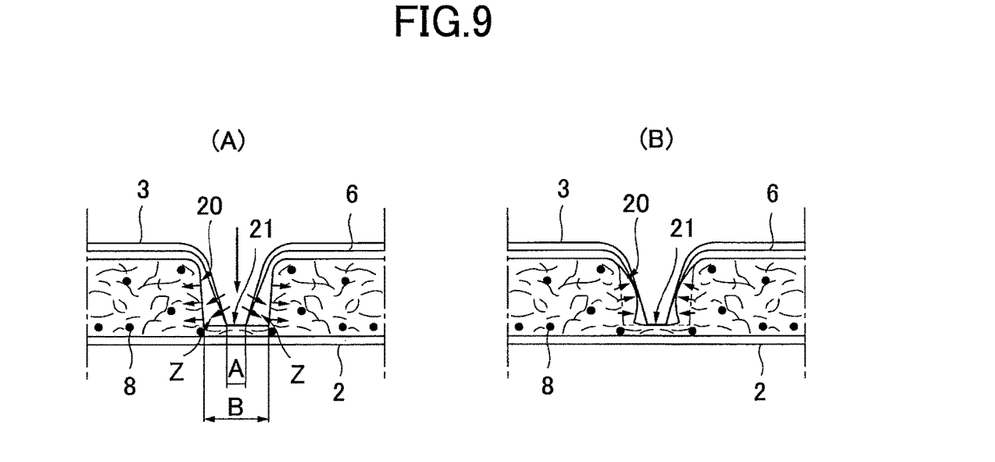
FIG. 9(A) is a cross-sectional view illustrating a permeable state of a body fluid.
FIG. 9(B) is a cross-sectional view illustrating an expanded state when absorbing a fluid.
Figure 10:
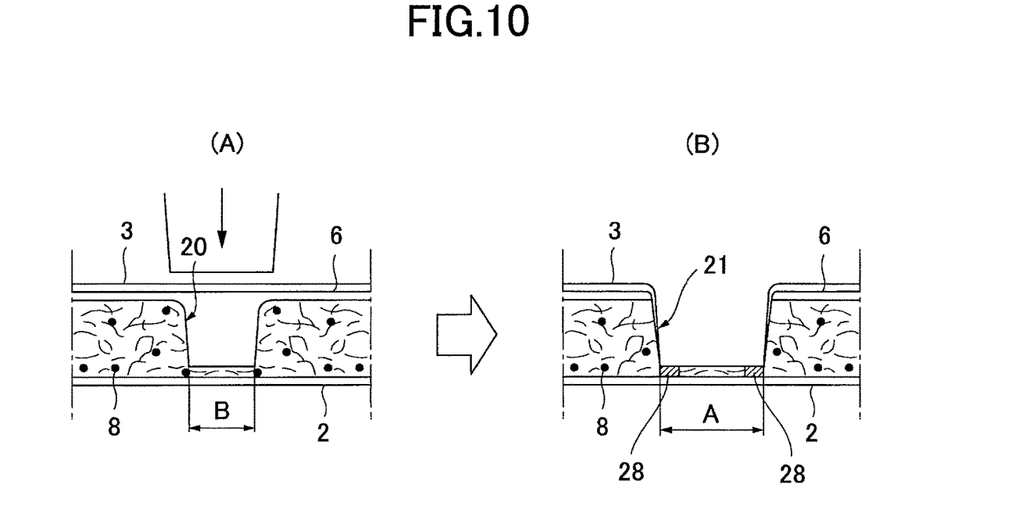
FIG. 10(A) is a cross-sectional view before forming an embossed pattern.
FIG. 10(B) is a cross-sectional view after forming the embossed pattern.

The embossed part 21 can be formed to be narrower than the absorbent body concave portion 20 with respect to the width direction of the pad (FIG. 9), or can be formed to be wider than the absorbent body concave portion 20, as described later (FIG. 10). Moreover, with respect to the longitudinal direction of the pad, the embossed part 21 can be formed with a small dimension, or can be formed so as to protrude. The embossed part 21 may be formed by just being pressed without being bonded with the bottom part of the absorbent body concave portion 20 by thermal fusion bonding. Otherwise, the embossed part 21 may be formed by bonding the liquid permeable topsheet 3 and the second sheet 6 with the absorbent body 4 by bonding the liquid permeable topsheet 3 and the second sheet 6 with a synthetic fiber contained in the absorbent body 4 by thermal fusion bonding or by ultrasonic welding.

In this manner, if the width A of the embossed part 21 is formed narrower than the width B of the absorbent body concave portion 20, as illustrated in FIG. 9(A), when a body fluid flowing on the surface of the liquid permeable topsheet 3 flows into the embossed part 21, the body fluid permeates the liquid permeable topsheet 3 and the second sheet 6 and is temporarily stored in buffer zones Z formed between side surfaces of the absorbent body concave portion 20 and the liquid permeable topsheet 3. After that, the body fluid is distributed distributes in the front-back direction along the absorbent body concave portion 20 and is absorbed and retained in the absorbent body 4 through the side surfaces of the absorbent body concave portion 20. Accordingly, even when large amounts of urine are expelled at one time, the urine can be quickly absorbed by being temporarily stored in the buffer zone Z.

In addition, because the absorbent body concave portion 20 is formed without being compressed, as illustrated in FIG. 9(B), when the body fluid permeates into the absorbent body concave portion 20 and the polymer 8 and the pulp around the absorbent body concave portion 20 expand due to the absorption of the body fluid, an elevation of the bottom is made smaller than that of the bottom including a high-density area of pulp or polymer formed by compression. Moreover, because the embossed part 21 that is embossed from the upper surface side of the liquid permeable topsheet 3 is provided corresponding to the absorbent body concave portion 21, even when both side surfaces of the absorbent body concave portion 20 swell inward, because the liquid permeable topsheet 3 provided in the absorbent body concave portion 20 acts to hold both of the side surfaces likely to expand, the expansion of both of the side surfaces can be reduced Accordingly, it is possible to prevent the absorption of the body fluid from decreasing due to blockage of the absorbent body concave portion 20 by the polymer 8 or the pulp that has expanded from absorption of the body fluid.

Furthermore, because the absorbent body concave portion 20 is formed by the fiber stacking or formed so as to have a laminate structure of the absorbents 4a, 4b without being compressed, consolidation of the absorbent body by the compression and hardening by the thermal fusion bonding do not occur, and the inherent flexibility of the absorbent body and the preferable wearing comfort can be maintained.

In addition, because the embossed part 21 is provided in the absorbent body concave portion 20 by being embossed from the upper surface side of the liquid permeable topsheet 3, the liquid permeable topsheet 3 is provided in the absorbent body concave portion 20, which makes it possible to maintain a structure allowing the absorbent body concave portion 20 to be unlikely to collapse even when an external force is applied and to rapidly absorb the body fluid.

As illustrated in FIG. 9(A), when the width A of the embossed part 21 is specifically formed so as to be smaller than the width B of the absorbent body concave portion 20 (A<B), the ratio A/B is preferably set at 0.5 or more but less than 1, and more preferably 0.5 or more but less than 0.8. This causes the buffer zones Z, Z, which temporarily store the permeated body fluid and become buffering areas when the superabsorbent polymer 8 or the pulp absorbs the body fluid and swells, to be properly formed between the side surfaces of the absorbent body concave portion 20 and the liquid permeable topsheet 3 (second sheet 6). Here, when the absorbent body concave portion 20 is formed into a concave groove shape, both of the side surfaces are sometimes formed into a sloping shape while considering a draft angle. In this case, the width on the bottom side (on the liquid impermeable backsheet 2 side) of the absorbent body concave portion 20 is adopted as the width B of the absorbent body concave portion 20.

In contrast, as illustrated in FIG. 10, the width A of the embossed part 21 can be formed larger than the width B of the absorbent body concave portion 20 by using an embossing machine having a tip wider than or equal to the width B of the absorbent body concave portion 20 (A≥B). In this case, as illustrated in FIG. 10(B), by providing the embossed part 21, high-density areas 28 obtained by compressing the absorbent body 4 are formed on both sided of the bottom part of the concave groove 22. This increases the stiffness of the concave groove 22 and increases the density gradient in its fiber density with the increasing distance from the center and with the decreasing distance to both side edges to be formed, which facilitates the diffusion of the absorbed body fluid from the center to both of the side edges by capillary action and makes it possible to rapidly transfer the body fluid from the concave groove 22 into the absorbent body 4.

[Other embodiments]

(1) In the above embodiments, although only a single concave groove 22 is formed at the center of the pad in the width direction, a plurality of separate concave grooves 22 extending in the longitudinal direction may be formed in the width direction. This causes the body fluid to distribute in the longitudinal direction and to be absorbed rapidly, thereby preventing the side leakage.

(2) In the above embodiments, although the highly compressed portion 23 is integrally provided in component members from the liquid permeable topsheet 3 to the absorbent body 4 by compressing all the members from the upper surface side of the liquid permeable topsheet 3, the highly compressed portion 23 may be formed in only the absorbent body 4 by compressing the absorbent body 4 from the upper surface side, or may be integrally provided for the encapsulating sheet and the absorbent body 4 by compressing the members from the upper surface side of the encapsulating sheet. By providing the highly compressed portion 23 at least for the absorbent body 4, the deformation of the concave groove while being worn can be prevented, and the body fluid can be easily distributed over the length of the groove.

DESCRIPTION OF THE REFERENCE NUMERALS 1 incontinence pad
2 liquid impermeable backsheet
3 liquid permeable topsheet 4 absorbent body
6 second sheet
7 side non-woven-fabric
8 superabsorbent polymer
10 inner standing gather
11 outer standing gather
12, 13 threadlike elastic stretchable member
20 absorbent body concave portion
21 embossed part
22 concave groove
23 highly compressed portion
24 unit portion
25 slanted element
26 arch element

The invention claimed is:

1. An absorbent article comprising:
 a liquid permeable topsheet;
 a backsheet;
 an absorbent body provided between the liquid permeable topsheet and the backsheet;
 a groove formed in a surface of the absorbent body on the liquid permeable topsheet side and extending along an approximately longitudinal direction of the groove; and
 a highly compressed portion formed in a bottom surface of the groove,
 wherein the highly compressed portion includes a slanted element in a unit formed by dividing the groove in a longitudinal direction of the groove, and is formed by substantially crossing the groove from one side edge to the other side edge so as to form a first pattern and is formed into a second pattern obtained by repeatedly inverting the first pattern of the highly compressed portion of the unit in the longitudinal direction, and
 wherein each of the first pattern and the second pattern in the slanted element includes double lines that are parallel to each other.

2. The absorbent article as claimed in claim 1, wherein the sloping element is composed of a straight line, a curved line or a combination thereof.

3. The absorbent article as claimed in claim 1, wherein the highly compressed portion includes an arch element extending from both ends of the sloping element or neighborhoods thereof in approximately the longitudinal direction and formed into an curved shape protruding outward in the width direction.

4. The absorbent article as claimed in claim 1, wherein the absorbent body has an absorbent body concave portion formed over a portion of the surface on the liquid permeable topsheet in a longitudinal direction of the absorbent article, the portion of the surface including a body fluid expelling area, and
 an embossed part including the highly compressed portion is formed along the absorbent body concave portion.

5. The absorbent article as claimed in claim 4, wherein the embossed part is narrower than the absorbent body concave portion.

6. The absorbent article as claimed in claim 4, wherein the embossed part is wider than the absorbent body concave portion, and high-density areas obtained by compressing the absorbent body are formed on both sides of the absorbent body concave portion by providing the embossed part.

7. The absorbent article as claimed in claim 1, wherein the double lines are formed so that the bottom surface of the groove has triangle shapes and parallelogram shapes arranged alternately in the longitudinal direction of the groove.

* * * * *